United States Patent [19]

Madding

[11] 4,454,324

[45] Jun. 12, 1984

[54] PROCESS FOR PRODUCTION OF ENCAINIDE

[75] Inventor: Gary D. Madding, Evansville, Ind.

[73] Assignee: Mead Johnson & Company, Evansville, Ind.

[21] Appl. No.: 481,218

[22] Filed: Apr. 1, 1983

Related U.S. Application Data

[62] Division of Ser. No. 330,298, Dec. 14, 1981, Pat. No. 4,394,507.

[51] Int. Cl.$^3$ ............................................ C07D 213/50
[52] U.S. Cl. ..................................................... 546/337
[58] Field of Search .......................................... 549/337

[56] References Cited

U.S. PATENT DOCUMENTS 3,931,195  1/1976  Dykstra et al. ............... 260/293.58
4,000,143 12/1976  Dykstra et al. ............... 260/293.67
4,064,254 12/1977  Dykstra et al. ...................... 424/267
4,104,274  8/1978  Connor et al. ....................... 546/337

OTHER PUBLICATIONS

A. H. Beckett et al., Jour. Pharm. and Pharmacol., vol. 2, No. 7 (1955) pp. 717–730.
I. Saito et al., Synthesis (1976) pp. 255–256.
M. Yamamoto et al., Chem. Pharm. Bull., 26/6, 1633–1651 (1978).
S. J. Dykstra et al., J. Med. Chem., vol. 16, 1015–1020 (1973).
J. E. Byrne et al., J. Pharmacology and Experimental Therapeutics, 200, 147–154 (1977).
H. Stephan et al., J. Chem. Soc., 4420–4421 (1956).
J. F. Wolfe et al., Journal of Organic Chemistry, vol. 39, 2006–1010 (1974).
R. Levine et al., J. Organic Chemistry, vol. 25, 530–537 (1960).
N. Goldberg et al., Journal American Chemical Society, vol. 74, 5217–5219 (1952).
N. Goldberg et al., Journal American Chemical Society, vol. 73, 4301–4303 (1951).

Primary Examiner—Norma S. Milestone
Attorney, Agent, or Firm—Richard P. Ryan; Robert H. Uloth

[57] ABSTRACT

An improved process for the preparation of 4-methoxy-2'-{2-(1-methyl-2-piperidyl)ethyl}benzanilide has been developed. The process comprises essentially three steps starting with methyl anthranilate and 2-picoline and features a novel low-pressure hydrogenation sequence.

3 Claims, No Drawings

PROCESS FOR PRODUCTION OF ENCAINIDE

CROSS REFERENCE TO RELATED APPLICATION

This application is a divisional of the pending application U.S. Ser. No. 06/330,298 filed Dec. 14, 1981, now U.S. Pat. No. 4,394,507.

BACKGROUND OF THE INVENTION

This invention describes an improved, more economical process for synthesis of encainide (I)

which is suitable for large scale manufacture. Encainide, chemically, 4-methoxy-2'-{2-(1-methyl-2-piperidyl)ethyl}benzanilide, is a member of a series of antiarrhythmic 2-phenethylpiperidines bearing amide substituents in the ortho-position of the phenyl ring. Encainide hydrochloride is also referred to in the literature as MJ 9067-1 (USAN and the USP Dictionary of Drug Names, 1980, p. 122, United States Pharmacopeal Convention, Inc., 12601 Twinbrook Parkway, Rockville, Md. 20852, Library of Congress Catalog Card No. 72-88571). Currently, encainide is undergoing clinical evaluation as an effective antiarrhythmic agent.

Previous synthesis of encainide and closely related compounds is described in the following references.

Dykstra, S. J., et al., *J. Med. Chem.*, 16, 1015–1020 (1973).

S. J. Dykstra and J. L. Minielli, U.S. Pat. No. 3,931,195 patented Jan. 6, 1967; U.S. Pat. No. 4,000,143 patented Dec. 28, 1978; U.S. Pat. No. 4,064,254 patented Dec. 20, 1977.

Byrne, J. E., et al., *J. Pharmacology and Experimental Therapeutics*, 200, 147–154 (1977).

The process, as disclosed in the above cited references, which has been used for preparation of encainide is shown in Scheme 1.

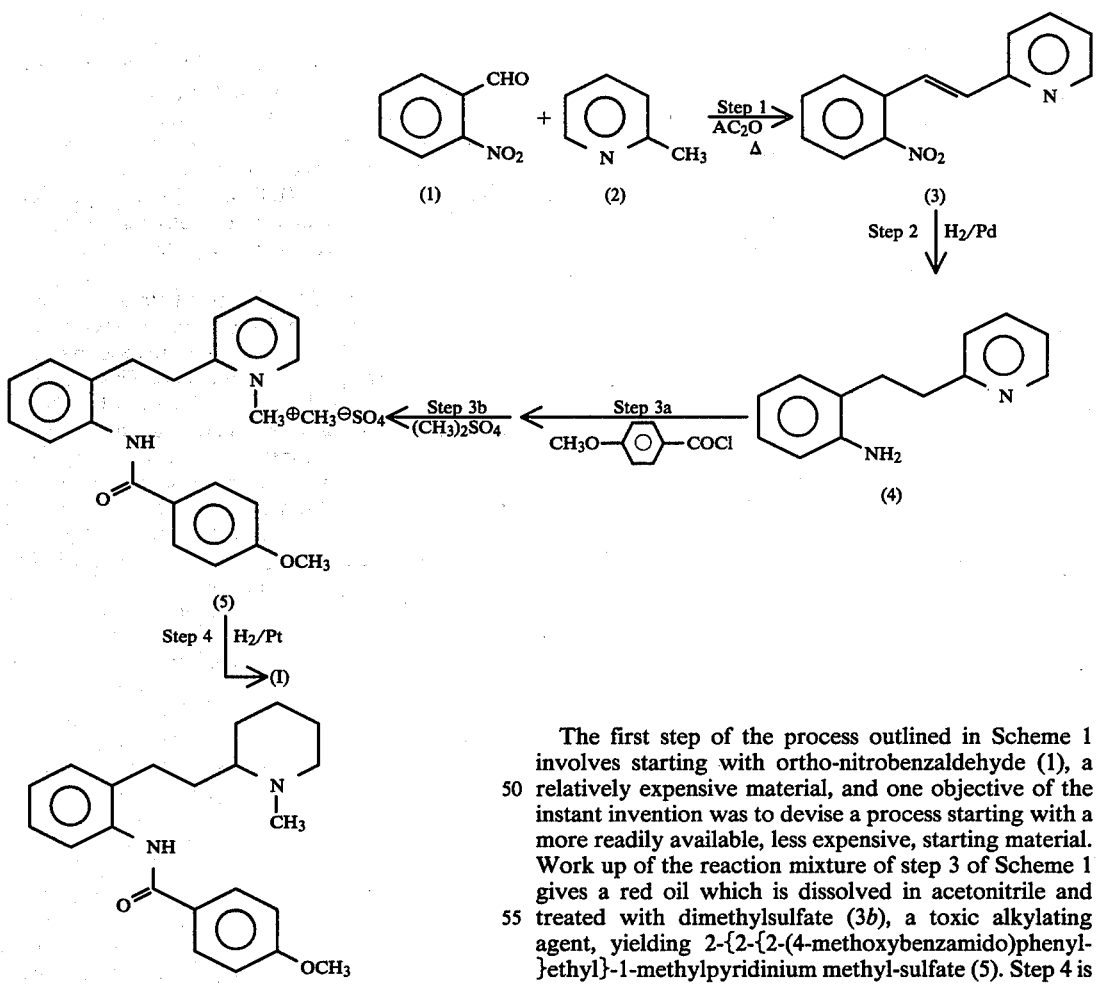

The first step of the process outlined in Scheme 1 involves starting with ortho-nitrobenzaldehyde (1), a relatively expensive material, and one objective of the instant invention was to devise a process starting with a more readily available, less expensive, starting material. Work up of the reaction mixture of step 3 of Scheme 1 gives a red oil which is dissolved in acetonitrile and treated with dimethylsulfate (3b), a toxic alkylating agent, yielding 2-{2-{2-(4-methoxybenzamido)phenyl}ethyl}-1-methylpyridinium methyl-sulfate (5). Step 4 is the hydrogenation of an alcoholic solution of (5) using a platinum catalyst.

The prior art method represented by Scheme 1 is thus a multiple step process using expensive and hazardous raw materials. In contrast, the process of the instant invention uses a less expensive commercially available starting material; requires less labor; avoids toxic alkylating agents; and, in total, provides high quality encainide at lower cost.

The following references relate to component steps of the instant process described herein.

1. H. Stephan and G. Wadge, *J. Chem. Soc.*, 4420 (1956). This reference describes methyl N-p-anisoyl anthranilate, an intermediate produced in the instant process.

2a. J. F. Wolfe, D. E. Portlock and D. J. Feuerbach, *Journal of Organic Chemistry*, 39, 2006–2010 (1974).

2b. R. Levine and S. Reynolds, *J. Organic Chemistry*, 25, 530–537 (1960).

2c. N. Goldberg and R. Levine, *Journal American Chemical Society*, 74, 5217–5219 (1952).

2d. N. Goldberg, L. Barkley, and R. Levine, *Journal American Chemical Society*, 73, 4301–4303 (1951).

These references describe the acylation of metalated methyl heteroaromatics with non-enolizable esters; addressing the scope, mechanism, and application of the reaction. The acylation of metalated 2-picoline in the instant process is one specific application of this reaction type.

SUMMARY OF THE INVENTION

This invention relates to an improved synthetic process which can be adapted for large-scale preparation of the antiarrhythmic agent encainide, chemically, 4-methoxy-2'-[2-(1-methyl-2-piperidyl)-ethyl]benzanilide. The instant process, which starts from methyl anthranilate, an inexpensive chemical of commerce; features a novel low-pressure hydrogenation sequence which converts a readily prepared precursor directly to encainide. The subject process comprises essentially three steps and offers advantages in economies of starting raw material and labor costs as well as increased suitability for use with standard larger-scale chemical process equipment.

DETAILED DESCRIPTION OF THE INVENTION

The following flow chart, Scheme 2, illustrates the preparation of encainide from readily available starting materials utilizing the instant process. Step 3 depicts the novel hydrogenation sequence.

Scheme 2

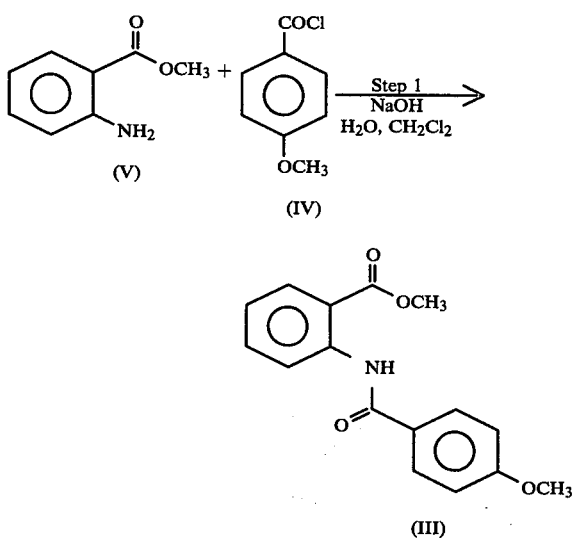

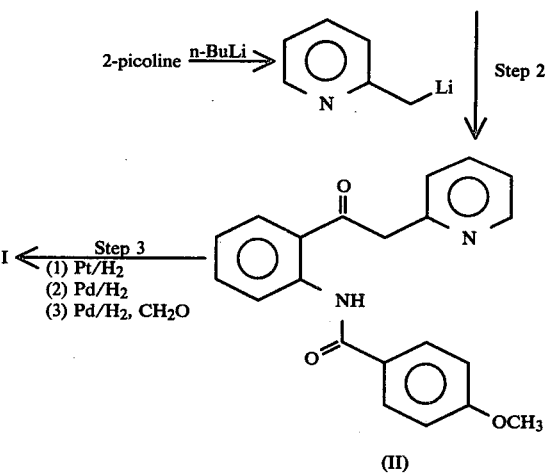

Step 1 of the scheme outlined above involves the reaction of methyl anthranilate (V) and p-anisoyl chloride (IV) to give the intermediate compound methyl N-p-anisoyl anthranilate (III). The starting materials for Step 1 are commercially available. Step 2 is accomplished by treating (III) with 2-picolyl lithium (prepared from 2-picoline, diisopropylamine, and n-butyl lithium) thereby yielding 2-(2-pyridyl acetyl)-p-anisanilide (II).

A conversion of the intermediate compound (II) to encainide (I) via Step 3 represents a novel hydrogenation sequence allowing the direct reduction of (II) to (I) without isolating any intermediate. This sequence consists of stirring the hydrochloride salt of (II) with $PtO_2$ under $H_2$ in glacial acetic acid at about room temperature until at least three equivalents of $H_2$ have been absorbed. The platinium catalyst is removed and replaced with added dry Pd/C catalyst and the resultant mixture stirred under $H_2$ with heating until two additional equivalents of $H_2$ have been absorbed. The mixture is then cooled to approximately room temperature, excess 37% formalin is added and the mixture is stirred until all $H_2$ absorption stops. Work up of the reaction mixture allows direct isolation of encainide hydrocloride. This hydrogenation sequence makes operable the instant process which produces encainide in good yield using readily available inexpensive starting materials. Additionally, this process is well suited for scaling up to large size chemical process equipment. The lesser requirement for handling of intermediates of the instant process compared to the older process reduces labor costs.

The entire synthesis of encainide as represented in the subject process is preferably carried out as a series of three steps going from the simplest starting materials (methyl anthranilate, p-anisoyl chloride, and 2-picoline) to encainide hydrochloride. The steps comprising the process are as follows:

(1) adding p-anisoyl chloride to a stirred chilled solution of methyl anthranilate and 50% sodium hydroxide in methylene chloride-water. The stirred reaction mixture is allowed to warm to room temperature to give methyl N-p-anisoyl anthranilate (III) in approximately 95% yield.

(2) adding (III) to a stirred cold solution of 2-picolyl lithium (pre-formed from n-butyl lithium, diisopropylamine, and 2-picoline) in a reaction inert solvent such as tetrahydrofuran. The stirred reaction mixture is allowed to warm to room temperature to give 2-(2-pyridylacetyl)-p-anisanilide (II).

(3) hydrogenating (II) in glacial acetic acid in the presence of a platinum catalyst, e.g. $PtO_2$ or carbon-support Pt, until hydrogen uptake reaches three equivalents; replacing the Pt catalyst with palladium-on-carbon catalyst and continuing hydrogenation until two more equivalents of hydrogen are absorbed; and then adding excess 37% formalin to the reaction mixture and continuing hydrogenation until all hydrogen absorption ceases. The catalyst is removed and the product (I) is isolated directly in approximately 75% yield.

DESCRIPTION OF SPECIFIC EMBODIMENTS

The process of this invention is illustrated in greater detail by the following examples directed to preferred embodiments of the hereinabove described process steps. These examples, however, should not be construed as limiting the scope of the present invention in any way.

EXAMPLE 1

Methyl N-p-Anisoylanthranilate (III)

A solution of 529.8 g (3.505 mole) methyl anthranilate and 294.4 g 50 weight percent NaOH (3.68 mole) in 3.6 L $CH_2Cl_2$ and 1.8 L $H_2O$ was stirred in an ice-bath as 627.8 g (3.680 mole) p-anisoyl chloride was added at such rate that the temperature did not exceed 10° C. (time required was 1.25 hr). The mixture was allowed to warm to 23° C. Acetic acid (50 mL) was added to adjust the pH to 5. The layers were separated and the organic layer was washed with 10% aqueous $NaHCO_3$ (1×0.8 L) and brine (1×0.8 L). The solvent was removed in vacuo. The residual white solid was recrystallized from 7.0 L boiling methanol. The product (III) was dried in vacuo at 70° C. for 24 hr to yield 959.7 g (96.0%) white crystalline solid, m.p. 122.5°–124.5° C.

EXAMPLE 2

2-(2-Pyridylacetyl)-p-anisanilide (II)

A dry, nitrogen purged flask was charged with 1.875 mL 1.6 N (3.0 mole) n-butyl lithium in hexane. The solution was stirred under nitrogen and chilled to −45° to −40° C., and 1.5 L THF (dried over molecular sieve 4 A) was added slowly. Diisopropylamine (303.6 g; 3.0 mole) was added at such a rate that the temperature did not exceed −30° C. Then 307.3 g (3.3 mole) 2-picoline was added with stirring, keeping the temperature below −30° C. The cooling was interrupted, and the mixture was slowly warmed to 10° C. by which time the conversion to anion was complete and all the 2-picolyl lithium had redissolved. The solution was recooled to −45° to −40° C. (the orange solid reprecipitated), and a solution of 285.3 g (1.0 mole) methyl N-p-anisoylanthranilate (III) in 1.9 L THF was added at a rate so the temperature did not exceed −30° C. After the addition, the mixture was slowly warmed to 25° C. The solution was adjusted to pH 6 with 500 mL acetic acid; 5.0 L $H_2O$ was added with stirring. Then the organic solvents were distilled in vacuo and the residual yellow semi-solid product was extracted with $CH_2Cl_2$ (1×2.5 L). The extract was washed with $H_2O$ (1×1.0 L) and stripped to dryness in vacuo. The residue was dissolved in 6.7 L boiling isopropanol. The solution was chilled with stirring to 5°±5° C., and the resulting yellow solid was collected on a filter, rinsed with isopropanol and dried in vacuo at 80° C. for six hours. The filtrate was concentrated and chilled to yield a second crop of product. Both crops of intensely yellow material exhibited single spots in the TLC (7.5 cm silica gel with indicator, 9 $CH_2Cl_2$:1 methanol, UV). The total yield was 306.7 g (88.5%) of material, m.p. 145°–148.5° C.

EXAMPLE 3

Large Scale Preparation of (II)

Charge a dry, nitrogen purged, 100 gallon stainless steel reactor with tetrahydrofuran (47 kg). Cool the THF to 5° C. or less. Slowly add 15% n-butyl lithium in hexane (37 kg×0.152=5.62 kg of n-butyl lithium; 87.6 mole) to the THF at a rate that will keep the reaction temperature below 5° C. Slowly add diisopropylamine (8.9 kg; 87.9 mole) to the mixture at a rate that wi l keep the reaction temperature below 5°. Slowly add 2-picoline (8.3 kg; 89.1 mole) to the reaction solution at a rate that maintains the reaction temperature at less than 5° C. In a separate reactor, dissolve the N-p-anisoyl anthranilate (7.7 kg; 27 mole) in warm (approximately 30° C.) THF (47 kg). Slowly add this solution to the 2-picolyl lithium mixture at a rate that will keep the reaction temperature below 10° C. After the addition is completed, the mixture is warmed to approximately 20° C. and stirred for 15 minutes. Charge a 500 gal. glass-lined reactor with $H_2O$ (135 kg) and acetic acid (13.5 kg; 224.6 mole). Cool the mixture to about 0° C. and add the THF solution to this chilled mixture. The $H_2O$ layer (bottom) is separated and washed with methylene chloride (2×58 kg). The organic layers are combined and concentrated in vacuo. Isopropanol (143 kg) is added, and the mixture is heated to reflux. The mixture is concentrated in vacuo to one-half volume and cooled to about 0° C. The solid is collected and washed with isopropanol (2×6 kg). The solid is dried at about 40° C. under vacuum to yield 8.25 kg (89%) of product (II).

EXAMPLE 4

2-(2-Pyridylacetyl)-p-anisanilide Hydrochloride (II Hydrochloride)

2-(2-Pyridylacetyl)-p-anisanilide (II) (25.0 g, 0.0722 mole) was dissolved with gentle warming in 500 ml THF. The bright yellow solution was chilled in an ice bath, and 6.5 ml (0.078 mole) 12 N HCl was added. The yellow color disappeared and a white precipitate formed immediately. The solid was collected on a filter; rinsed with THF and air-dried to give 27.4 g white solid (99.3%), m.p. 190.5°–191.5° (dec.).

EXAMPLE 5

4-Methoxy-2'-[2-(1-methyl-2-piperidyl)ethyl]benzanilide (I), Encainide

A mixture of 53.5 (0.1397 mole) 2-(2-pyridylacetyl)-p-anisanilide hydrochloride, 1.0 g platinum catalyst (2.5-5% Pt/C or $PtO_2$) and 1.0 L glacial acetic acid was stirred vigorously under a slight positive pressure of $H_2$ at 23°–25° C. for 20 hr, by which time 0.43 mole (3.08 equivalents) of $H_2$ had been absorbed. The catalyst was removed by filtration through a celite bed. The filtrate was returned to the flask, and 10.0 g 10% Pd/C was added under nitrogen. The mixture was stirred vigorously under $H_2$ as it was heated to 60°±3° C. After an additional 6.5 hr the total $H_2$ uptake equaled 0.71 mole (5.08 equivalents, 101.6% of theory). The mixture was cooled to 25° C., and 22.7 g formalin (37 weight percent formaldehyde, 8.4 g, 0.28 mole) was injected into the reaction mixture. The mixture was stirred vigorously under H₂ at 23°–25° C. for 20 hr; during that time 0.1452 mole (1.04 equivalents) H₂ was absorbed. The catalyst was removed by filtration, and the filtrate concentrated in vacuo to a thick oil. Twice the oil was mixed with 200 mL isopropanol and stripped in vacuo at 90° C. to a thick oil. The oil was dissolved in 200 mL boiling isopropanol. The solution was stirred, seeded with (I), and chilled to 10° C. for 1 hr. The solid was collected on a filter, rinsed with cold isopropanol (2×2.0 mL) to give 36.6 g (67.4%) product, m.p. 181.5°–184.5° C. Additional product was obtained from isopropanol filtrate to give a total yield of 76.1% encainide.

What is claimed is:

1. The compound, 2-(2-pyridylacetyl)-p-anisanilide and its acid addition salts.

2. The compound of claim 1, 2-(2-pyridylacetyl)-p-anisanilide.

3. The compound of claim 1, 2-(2-pyridylacetyl)-p-anisanilide hydrochloride.

* * * * *